(12) United States Patent
Goodarznia et al.

(10) Patent No.: US 12,209,067 B2
(45) Date of Patent: Jan. 28, 2025

(54) OXIDATIVE DEHYDROGENATION PROCESS

(71) Applicant: NOVA CHEMICALS (INTERNATIONAL) S.A., Fribourg (CH)

(72) Inventors: Shahin Goodarznia, Calgary (CA); Vasily Simanzhenkov, Calgary (CA); Mohamed Aiffa, Calgary (CA); Bolaji Olayiwola, Calgary (CA)

(73) Assignee: NOVA Chemicals (International) S.A., Fribourg (CH)

(*) Notice: Subject to any disclaimer, the term of this patent is extended or adjusted under 35 U.S.C. 154(b) by 0 days.

(21) Appl. No.: 18/025,556

(22) PCT Filed: Sep. 20, 2021

(86) PCT No.: PCT/IB2021/058554
§ 371 (c)(1),
(2) Date: Mar. 9, 2023

(87) PCT Pub. No.: WO2022/069995
PCT Pub. Date: Apr. 7, 2022

(65) Prior Publication Data
US 2023/0348343 A1    Nov. 2, 2023

Related U.S. Application Data

(60) Provisional application No. 63/084,628, filed on Sep. 29, 2020.

(51) Int. Cl.
*C07C 5/333* (2006.01)
*B01J 19/00* (2006.01)

(52) U.S. Cl.
CPC ......... *C07C 5/3332* (2013.01); *B01J 19/0033* (2013.01); *C07C 2521/04* (2013.01)

(58) Field of Classification Search
CPC .. C07C 5/48; C07C 5/333; C07C 1/24; C07C 11/04; C07C 5/3332; C07C 51/235; B01J 27/0576; B01J 19/00; B01J 19/0033
See application file for complete search history.

(56) References Cited

U.S. PATENT DOCUMENTS

| 5,550,309 A * | 8/1996 | Maunders ............... C01B 3/503 585/654 |
| 11,053,179 B2 * | 7/2021 | Olayiwola ........... B01J 23/6482 |
| 2004/0225164 A1 | 11/2004 | Allison et al. |

FOREIGN PATENT DOCUMENTS

WO    WO 2020/079639    4/2020

OTHER PUBLICATIONS

Kaddouri et al., "Oxidative dehydrogenation of ethane on the alpha and beta phases of NiMoO4", Catalysis Today, Elsevier, Amsterdam, NL, Apr. 17, 1998, 40(2-3):201-206.

PCT International Search Report and Written Opinion in International Appln. No. PCT/IB2021/058554, mailed on Dec. 14, 2021, 8 pages.

* cited by examiner

*Primary Examiner* — Sharon Pregler
(74) *Attorney, Agent, or Firm* — Fish & Richardson P.C.

(57) ABSTRACT

The product distribution from an oxidative dehydrogenation process can be altered by co-feeding different ratios of ethanol to steam, in the range of 0.01 to 0.50 ethanol:steam to an oxidative dehydrogenation reactor. Increasing the ethanol to steam ratio was found to: increase ethylene yield; decrease acetic acid yield; increase, or decrease, or cause no effect on CO or $CO_2$ yield; and have negligible effect on ethane conversion. The feed ethanol is converted to carbonaceous products without negatively effecting the catalyst activity.

32 Claims, No Drawings

OXIDATIVE DEHYDROGENATION PROCESS

CLAIM OF PRIORITY

This application is a National Stage Application under 35 U.S.C. § 371 and claims the benefit of International Application No. PCT/IB2021/058554, filed Sep. 20, 2021, which claims priority to U.S. Provisional Application No. 63/084,628 filed on Sep. 29, 2020, the entire contents of which are hereby incorporated by reference

TECHNICAL FIELD

The present specification is directed to an oxidative dehydrogenation process to produce olefins. In particular, the process involves an oxidative dehydrogenation process of ethane to ethylene using ethanol and steam in the feed stream.

BACKGROUND ART

Catalytic oxidative dehydrogenation (ODH) of alkanes into corresponding alkenes is an alternative to steam cracking, the method of choice for the majority of today's commercial-scale olefin producers. Despite its widespread use, steam cracking has its downsides. Steam cracking is energy intensive, requiring temperatures in the range of 700° C. to 1000° C. to satisfy the highly endothermic nature of the cracking reactions, results in production of significant amounts of greenhouse gasses, and is expensive owing to the high fuel demand, the requirement for reactor materials that can withstand the high temperatures, and the necessity for separation of unwanted by-products using downstream separation units. Also, the production of coke by-product requires periodic shutdown for cleaning and maintenance, and the selectivity for ethylene is only around 80-85% for a conversion rate that does not generally exceed 60%.

In contrast to steam cracking, ODH operates at lower temperatures, produces insignificant amounts of greenhouse gases, does not produce coke, and using newer-developed catalysts provides selectivity for ethylene of over 85% at close to 60% conversion. However, like stream cracking, ODH may result in the production of unwanted by-products. For example, ODH of ethane results in the production of acetic acid which requires separation of the target product ethylene. It is an object of the present disclosure to control the degree to which acetic acid is produced in the oxidative dehydrogenation of ethane.

SUMMARY OF INVENTION

The oxidative dehydrogenation product distribution can be altered by means of co-feeding, along with an ethane and oxygen, different ratios of ethanol to steam, in the range of 0.01 to 0.50 ethanol:steam to an oxidative dehydrogenation reactor. Increasing the ethanol to steam ratio in the reported range was found to: increase ethylene yield; decrease acetic acid yield; increase, or decrease, or cause no effect on CO or $CO_2$ yields; and have negligible effect on ethane conversion. The feed ethanol is converted to carbonaceous products without negatively affecting the catalyst activity.

Provided in this disclosure is a process for the oxidative dehydrogenation of ethane into ethylene comprising:
 providing a combined feed comprising ethane, oxygen, steam, and ethanol, and optionally a heat removal diluent gas, to an ODH reactor;
 contacting the combined feed with an ODH catalyst in the ODH reactor under ODH conditions to form ethylene;
 wherein the combined feed comprises from 0.05 vol. % to 5 vol. % ethanol; and
 wherein the volumetric ratio of ethanol to steam in the combined feed is between from 0.01 to 0.50, preferably from 0.01 to 0.25, more preferably from 0.02 to 0.10.

Also provided in this disclosure is a process for increasing ethylene yield from an oxidative dehydrogenation (ODH) reactor system, the ODH reactor system comprising at least one ODH reactor, the at least one ODH reactor containing at least one bed of mixed metal oxide catalyst, the process comprising:
 forming a feed stream comprising ethane, oxygen, and an optional heat removal diluent gas;
 forming an ethanol/steam stream comprising ethanol and steam and an optional heat removal diluent gas;
 heating the ethanol/steam stream to a temperature above the dew point of ethanol;
 co-feeding the heated ethanol/steam stream and the feed stream as a combined feed to the at least one ODH reactor; and
 contacting the combined feed with the at least one bed of mixed metal oxide catalyst under ODH conditions to form ethylene;
 wherein the combined feed comprises from 0.01 vol. % ethanol to 5.0 vol % ethanol;
 wherein the volumetric ratio of ethanol to steam in the combined feed is from 0.01 to 0.50; and
 wherein the ethylene yield is increased compared to the same process and oxidative dehydrogenation reactor system wherein the combined stream does not comprise ethanol.

In some embodiments, the processes include a volumetric ratio of ethanol to steam in the combined feed of from 0.01 to 0.25. In some embodiments, the volumetric ratio of ethanol to steam in the combined feed is from 0.02 to 0.10.

In some embodiments, the combined feed comprises from 0.1 vol. % to 3 vol. % ethanol, preferably from 0.5 vol. % to 2 vol. % ethanol.

In some embodiments, the combined feed comprises from 1 vol. % to 30 vol. % oxygen, preferably from 3 vol. % to 25 vol. % oxygen, more preferably from 5 vol. % to 20 vol. % oxygen In some embodiments, the combined feed comprises from 1 vol. % to 30 vol. % ethane, preferably from 15 vol. % to 70 vol. % ethane, more preferably from 20 vol. % to 50 vol. % ethane.

In some embodiments, the ODH reactor system includes at least two ODH reactors. In some embodiments, the ODH reactor system includes at least two mixed metal oxide catalysts.

In some embodiments, the ODH conditions comprise a temperature from about 300° C. to about 500° C. In some embodiments, the ODH conditions comprise a temperature from about 300° C. to about 425° C. In some embodiments, the ODH conditions comprise a temperature from about 300° C. to about 400° C. In some embodiments, the ODH conditions comprise a temperature from about 310° C. to about 350° C. In some embodiments, the ODH conditions comprise an inlet pressure from about 0.5 psig to about 100 psig. In some embodiments, the ODH conditions comprise an inlet pressure from about 15 psig to about 50 psig. In some embodiments, the ODH conditions comprise a residence time from about 0.002 to about 72 seconds. In some embodiments, the ODH conditions comprise a residence time from about 0.1 to about 10 seconds. In some embodiments, the ODH conditions comprise a gas hourly space velocity from about 50 to about 2,000,000 h$^{-1}$. In some embodiments, the ODH conditions comprise a gas hourly space velocity from about 500 to about 6,000 h$^{-1}$.

In some embodiments, the feed stream is outside the flammability envelope.

In some embodiments the ethanol reacts with oxygen to form acetic acid. In some embodiments, the ethanol dehydrates to form ethylene.

In some embodiments, the process includes having a production rate of acetic acid that is decreased from a process in which only the feed stream is fed to the oxidative dehydrogenation reactor system. In some embodiments, co-feeding the ethanol/steam stream with the feed stream to the oxidative dehydrogenation reactor system yields a production rate of acetic acid that remains the same as a process in which only the feed stream is fed to the oxidative dehydrogenation reactor system.

In some embodiments, at least one ODH reactor includes a fixed bed type reactor. In some embodiments, at least one ODH reactor comprises a fluidized bed type reactor. In some embodiments, at least one ODH reactor comprises a moving bed type reactor. In some embodiments, at least one ODH reactor comprises an ebulliated bed type reactor. In some embodiments, at least one ODH reactor comprises a shell and tube reactor design. In some embodiments, at least one ODH reactor comprises a tube reactor design.

In some embodiments, the mixed metal oxide catalyst or ODH catalyst is selected from the group consisting of:
) catalysts of the formula:

$$Mo_aV_bTe_cNb_dPd_eO_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the metals present in the catalyst;

ii) catalysts of the formula:

$$Ni_gA_hB_iD_jO_f$$

wherein: g is a number from 0.1 to 0.9, preferably from 0.3 to 0.9, most preferably from 0.5 to 0.85, most preferably 0.6 to 0.8; h is a number from 0.04 to 0.9; i is a number from 0 to 0.5; j is a number from 0 to 0.5; and f is a number to satisfy the valence state of the metals present in the catalyst; A is selected from the group consisting of Ti, Ta, V, Nb, Hf, W, Y, Zn, Zr, Si and Al or mixtures thereof; B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is selected from the group consisting of Ca, K, Mg, Li, Na, Sr, Ba, Cs, and Rb and mixtures thereof; and O is oxygen;

iii) catalysts of the formula:

$$Mo_aE_kG_lO_f$$

wherein: E is selected from the group consisting of Ba, Be, Ca, Cr, Mn, Nb, Ta, Ti, Te, V, W and mixtures thereof; G is selected from the group consisting of Al, Bi, Ce, Co, Cu, Fe, K, Mg, V, Ni, P, Pb, Sb, Si, Sn, Ti, U, and mixtures thereof; a=1; k is 0 to 2; 1=0 to 2, with the proviso that the total value of 1 for Co, Ni, Fe and mixtures thereof is less than 0.5; and f is a number to satisfy the valence state of the metals present in the catalyst;

iv) catalysts of the formula:

$$V_mMo_nNb_oTe_pMe_qO_f$$

wherein: Me is a metal selected from the group consisting of Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the metals present in the catalyst; and v) catalysts of the formula:

$$Mo_aV_rX_sY_tZ_uM_vO_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0; r=0.05 to 1.0; s=0.001 to 1.0; t=0.001 to 1.0; u=0.001 to 0.5; v=0.001 to 0.3; and f is a number to satisfy the valence state of the metals present in the catalyst.

In some embodiments, the mixed metal oxide catalyst comprises a mixed metal oxide selected from the group according to the formula:

$$Mo_1V_{0.1-1}Nb_{0.1-1}Te_{0.1-0.2}X_{0-0.2}O_f$$

wherein X is selected from Pd, Sb, Ba, Al, W, Ga, Bi, Sn, Cu, Ti, Fe, Co, Ni, Cr, Zr, Ca and oxides and mixtures thereof, and f is a number to satisfy the valence state of the metals present in the catalyst.

In some embodiments, the mixed metal oxide catalyst is diluted with stainless steel, alumina or a combination thereof.

DESCRIPTION OF EMBODIMENTS

Certain exemplary aspects of the present disclosure will now be described to provide an overall understanding of the principles of the process disclosed herein. Those of ordinary skill in the art will understand that the processes described herein are non-limiting exemplary aspects and that the scope of the various examples of the present disclosure is defined more particularly in the claims. The features illustrated or described in connection with one exemplary aspect may be combined with the features of other aspects. Such modifications and variations are intended to be included within the scope of the present disclosure.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present invention desires to obtain. At the very least, and not as an attempt to limit the application of the doctrine of equivalents to the scope of the claims, each numerical parameter should at least be construed in light of the number of reported significant digits and by applying ordinary rounding techniques.

As used herein, "ethanol/steam stream" refers to a stream that includes ethanol and steam.

As used herein, "conversion" refers to the percentage of ethane carbon atoms in the feed that are converted to carbonaceous products, and can be calculated according to the formula:

$$\text{Conversion (\%)} = \frac{\dfrac{\text{Net mass flow rate of converted } C_2H_6(\text{g } C_2H_6/\text{min})}{\text{Molecular weight of } C_2H_6(\text{g } C_2H_6/\text{mol } C_2H_6)}}{\dfrac{\text{Mass flow rate of feed } C_2H_6(\text{g } C_2H_6/\text{min})}{\text{Molecular weight of } C_2H_6(\text{g } C_2H_6/\text{mol } C_2H_6)}} \times 100$$

where the net mass flow of converted $C_2H_6$ refers and is equal to the mass flow rate of $C_2H_6$ in the product stream minus the mass flow rate of $C_2H_6$ in the feed stream.

As used herein, "selectivity" refers to the percentage of ethane carbon atoms that are converted to a specific product X in the oxidative dehydrogenation process. For example, a selectivity of 50% for ethylene indicates 50% of the ethane carbon atoms that are converted during the oxidative dehydrogenation process are converted into ethylene. Selectivity, is calculated according to the formula:

$$\text{Selectivity (\%)} = \frac{\dfrac{\text{Net mass flow rate of } X(\text{g } X/\text{min})}{\text{Molecular weight of } X(\text{g } X/\text{mol } X)}}{\left[\dfrac{\text{Net mass flow rate of converted } C_2H_6(\text{g } C_2H_6/\text{min})}{\text{Molecular weight of } C_2H_6(\text{g } C_2H_6/\text{mol } C_2H_6)}\right] * \dfrac{\text{Mol. Equiv. of } X}{\text{mol } C_2H_6}}$$

where X is the product that is being assessed, the net mass flow rate refers to flow in g/min for X or converted $C_2H_6$ and is equal to the mass flow rate of X or converted $C_2H_6$ in the product stream minus the mass flow rate of component X or converted $C_2H_6$ in the feed stream, and molar equivalent (Mol. Equiv.) refers to the amount of X, in moles, that reacts completely with or is produced by one mole of ethane. If the sum of all selectivities for products derived from conversion of ethane did not total 100%, the selectivities were normalized to 100%. Normalization for each product can be calculated by dividing the selectivity for that product by the sum of all carbon atom product selectivities.

As used herein, "carbonaceous product" refers to any product compound that has a carbon atom present in its molecular structure.

As used herein, "co-feeding" refers to feeding at least two streams simultaneously, the streams being previously mixed or separate.

As used herein, "dew point" refers to the temperature, at a given pressure, at which the components of any gas mixture will start to condense out of the gaseous phase.

As used herein, "feed stream" refers to a mixture provided to an oxidative dehydrogenation reactor, that includes not less than 20 vol % of ethane, up to 30 vol % oxygen, and the balance a heat removal diluent gas which is selected from inert gases, N2, $CO_2$, and steam.

As used herein, "flammability envelope" refers to the envelope defining the flammability zone in mixtures of fuel, oxygen and with or without a heat removal diluent gas.

As used herein, "gas hourly space velocity" (abbreviated GHSV) refers to the ratio of the gas volumetric flow rate where the gas includes the reacting gas species and an optional heat removal diluent gas at standard conditions (i.e., 0° C., 1 bar) to the volume of the catalyst bed. The catalyst bed can refer to either the catalyst active phase, or to the total catalyst formulation which can include such things as catalyst additives or promoters.

As used herein, "linear velocity" refers to the flow rate of the combined feed divided by the cross-section of the reactor divided by the void fraction of the catalyst bed. The flow rate of the combined feed is measured where the constituents in the combined feed first contact the catalyst and at the temperature and pressure at that point. The cross-section of the reactor is also measured at the entrance of the catalyst bed. The void fraction of the catalyst bed is defined as the volume of voids in the catalyst bed/total volume of the catalyst bed. The volume of voids refers to the voids between catalyst particles and does not include the volume of pores inside the catalyst particles.

As used herein, "heat removal diluent gas" refers to a gas that dilutes a stream and can remove heat from the stream.

As used herein, "mixed metal oxide catalyst" refers to a catalyst that can be used in an oxidative dehydrogenation reactor to oxidatively dehydrogenate ethane to ethylene.

As used herein, "residence time" refers to how much time material that is flowing through a volume spends in the volume. The residence times indicated herein are equal to the volumetric flow rate of the feed stream at standard conditions (i.e., 0° C., 1 bar) divided by volume of the reactor. Direct correlation of the measured residence times under operating conditions to residence time under standard conditions falls within the knowledge of the person skilled in the art.

As used herein, "weight hourly space velocity" (abbreviated WHSV) refers to the ratio of the gas mass flow rate where the gas includes the reacting gas species and an optional heat removal diluent gas to the mass of the catalyst bed. The catalyst bed can refer to either the catalyst active phase, or to the total catalyst formulation which can include such things as catalyst additives or promoters.

Embodiments of the disclosure are directed to increasing product flexibility in the ODH reactor system by feeding different feed ratios of ethanol to steam. The ODH reactor system includes at least one ODH reactor, which in turn includes at least one mixed metal oxide catalyst which can affect the conversion of ethane to ethylene. Some aspects of the disclosure are directed to a low-temperature reaction (e.g., below 500° C.) that produces ethylene from ethane and that may generate byproducts, such as carbon monoxide (CO), carbon dioxide ($CO_2$), and acetic acid. A low-temperature ODH catalyst may be utilized.

The ODH reactor system may include at least two ODH reactors, arranged either in series or in parallel or any combination thereof.

The ODH reactor may be a fixed-bed reactor (e.g., a tubular fixed-bed reactor), a fluidized-bed reactor, a moving bed reactor, an ebulliated bed reactor, a shell and tube reactor, or a tube type reactor, and so on. The reactors or reactor system generally utilize a heat-transfer fluid for removing heat from the reactor for temperature control of the reactor. The heat transfer (cooling) medium can be, as a non-limiting example, an oil, pressurized water or a molten salt.

For a fixed-bed reactor, reactants may be introduced into the reactor at one end and flow past an immobilized catalyst. Products are formed and an effluent having the products may discharge at the other end of the reactor. The fixed-bed reactor may have one or more tubes (e.g., ceramic tubes) each having a bed of catalyst and for flow of reactants and products. The tubes may include, for example, a steel mesh. Moreover, a heat-transfer (e.g., cooling) jacket adjacent the tube(s) may provide for temperature control of the reactor. The aforementioned heat transfer fluid may flow through the reactor jacket.

For a fluidized bed reactor, the reactor may have a support for the ODH catalyst. The support may be a porous structure or distributor plate and disposed in a bottom portion of the reactor. Reactants may flow upward through the support at a velocity to fluidize the bed of ODH catalyst (e.g., the catalyst rises and begins to swirl around in a fluidized manner). The reactants are converted to products upon contact with the fluidized catalyst. An effluent having products may discharge from an upper portion of the reactor. The fluidized bed reactor may have heat-transfer (e.g., cooling) tubes, or heat pipe, or a jacket to facilitate temperature control of the reactor. The aforementioned heat transfer fluid may flow through the reactor tubes or jacket. Lastly, the fluidized bed reactor can be a non-circulating fluidized bed, or a circulating fluidized bed, with or without a regenerator.

The combined feed to the ODH reactor includes from 10 vol. % to 80 vol. % ethane, preferably from 15 vol. % to 70 vol. % ethane, more preferably from 20 vol. % to 50 vol. % ethane, and from 1 vol. % to 30 vol. % oxygen, preferably from 3 vol. % to 25 vol. % oxygen, more preferably from 5 vol. % to 20 vol. % oxygen, and with or without a heat removal diluent gas which is selected from inert gases, $N_2$, $CO_2$, steam, and combinations thereof. The oxygen and alkane components can be fed separately to the reactor or as a combined stream, an effect that would be apparent to a person skilled in the art.

The present disclosure describes how the addition of an ethanol/steam stream that includes ethanol and steam and an optional heat removal diluent gas to the ODH reactor can provide a substantial improvement over adding only the feed stream to the ODH reactor. The ethanol/steam stream can be fed to the ODH reactor as a separate feed, or the ethanol/steam stream can be added to the feed stream which feeds the ODH reactor, or the ethanol/steam stream can be split between a separate feed and adding to the feed stream both of which feed the ODH reactor.

The ethanol/steam stream includes water in the form of steam. The volumetric ratio of ethanol to steam is in the range of 0.01 to 0.50, in some cases in the range of 0.01 to 0.25, in other cases in the range of 0.01 to 0.10. When forming an ethanol/steam stream, as opposed to combining all reactants in a single combined feed, it would be apparent to a person skilled in the art that in order to maintain the volumetric ratio the feed stream cannot use water as a heat removal diluent gas if the effect is to change the volumetric ratio of ethanol to steam in the combined feed such that it falls outside the stated limits (e.g. lower than 0.01).

The optional heat removal diluent gas in the ethanol/steam stream can include $N_2$, $CO_2$, or another heat removal diluent gas, or a mixture of heat removal diluent gases.

The ethanol/steam stream should be above its dew point temperature prior to being fed to the ODH reactor. The temperature of the ethanol/steam stream can be increased by heating the ethanol/steam stream above its dew point. If at least part of the ethanol/steam stream is added to the feed stream which feeds the ODH reactor, the temperature of the combined ethanol/steam stream and feed stream which feeds the ODH reactor should be above the dew point temperature of ethanol.

When an ethanol/steam stream is added to an ODH reactor producing ethylene, the addition of an ethanol/steam stream can both increase ethylene yield and decrease the acetic acid yield. In some cases, the addition of an ethanol/steam stream may have no effect on either CO or $CO_2$ yield, and have negligible effect on ethane conversion. The addition of an ethanol/steam stream may have a negligible effect on the ODH catalyst activity.

Operating conditions for the ODH process (ODH conditions) are within the knowledge of the person skilled in the art and include parameters such as temperature, pressure, flow rate, and residence times. The temperature in the ODH reactor can be measured by any means known in the art, such as by using thermocouples. The temperature in the ODH reactor can be below 500° C., in particular from 300° C. to 450° C. In some cases the temperature in the ODH reactor can be from 300° C. to 425° C., in other cases the temperature in the ODH reactor can be from 300° C. to 400° C., and in many cases the temperature in the ODH reactor can be from 310° C. to 350° C.

The inlet pressure in the ODH reactor can be measured by any means known in the art. The pressure in the ODH reactor can be below 100 psig, in particular from ambient pressure to 100 psig. In some cases the pressure in the ODH reactor is from 0.5 psig to 100 psig. In other cases the pressure in the ODH reactor is from 15 to 50 psig.

The residence time in the ODH reactor is a measure of how much time material that is flowing through the ODH reactor spends in the ODH reactor. The residence time in the ODH reactor can be from 0.002 seconds to 72 seconds and in some cases the residence time in the ODH reactor can be from 0.1 to 10 seconds.

The gas hourly space velocity (GHSV) can be estimated knowing the ratio of the gas volumetric flow rate where the gas includes the reacting gas species and an optional heat removal diluent gas at standard conditions (i.e., 0° C., 1 bar) and dividing by the volume of the active phase of the catalyst bed. The GHSV can be between 50 and 500,000 $h^{-1}$. In some cases, the GHSV is between 250 and 20,000 $h^{-1}$. In some cases, the GHSV is between 500 and 6,000 $h^{-1}$.

The linear velocity of the combined feed can be between 0.1 cm/sec to 10,000 cm/sec. In some embodiments, the linear velocity may be between 5 cm/sec to 1,000 cm/sec. In some embodiments, the linear velocity may be between 10 cm/sec to 200 cm/sec.

The weight hourly space velocity (WHSV) of the combined feed may be between 0.5 $h^{-1}$ and 50 $h^{-1}$. In some embodiments, the WHSV of the combined feed may be between 1.0 $h^{-1}$ and 25.0 $h^{-1}$. In some embodiments, the WHSV of the combined feed may be between 2.0 $h^{-1}$ and 10 $h^{-1}$.

The flammability envelope defines the flammability zone. It is often desirable to operate outside of the flammability envelope to decrease the safety and operability risks of the ODH reactor system.

The ODH reactor contains an ODH catalyst. In some cases, a secondary reactor contains an ODH catalyst. The ODH catalyst in the second reactor may be the same catalyst or catalyst type as the ODH catalyst in a first reactor. The catalyst may be a low temperature catalyst that includes molybdenum (Mo), vanadium (V), tellurium (Te), niobium (Nb), and oxygen (O) wherein the molar ratio of Mo to V is from 1:0.12 to 1:0.49, the molar ratio of Mo to Te is from 1:0.01 to 1:0.30, the molar ratio of Mo to Nb is from 1:0.01 to 1:0.30, and oxygen is present at least in an amount to satisfy the valency of any present metals. The molar ratios of Mo, V, Te, Nb can be determined by inductively coupled plasma mass spectrometry (ICP-MS). The catalyst may be a low temperature catalyst which provides for an ODH reaction at less than 450° C., in some cases less than 425° C., or in other cases less than 400° C.

Any of the mixed metal oxide catalysts used as an ODH catalyst known in the art are suitable for use in the methods disclosed herein. Non-limiting examples of suitable oxidative dehydrogenation catalyst include those containing one or more mixed metal oxides selected from:

i) catalysts of the formula:

$$Mo_aV_bTe_cNb_dPd_eO_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the metals present in the catalyst;

ii) catalysts of the formula:

$$Ni_gA_hB_iD_jO_f$$

wherein g is a number from 0.1 to 0.9, in many cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to at least satisfy the valence state of the metals in the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$Mo_aE_kG_lO_f$$

wherein E is chosen from Ba, Be, Ca, Cr, Mn, Nb, Ta, Ti, Te, V, W and mixtures thereof; chosen from Al, Bi, Ce, Co, Cu, Fe, K, Mg, V, Ni, P, Pb, Sb, Si, Sn, Ti, U, and mixtures thereof; a=1; k is 0 to 2; 1=0 to 2, with the proviso that the total value of 1 for Co, Ni, Fe and mixtures thereof is less than 0.5; and f is a number to at least satisfy the valence state of the metals in the catalyst;

iv) catalysts of the formula:

$$V_mMo_nNb_oTe_pMe_qO_f$$

wherein Me is chosen from Ta, Ti, W, Hf, Zr, Sb and mixtures thereof; m is from 0.1 to 3; n is from 0.5 to 1.5; o is from 0 to 3; p is from 0.001 to 5; q is from 0 to 2; and f is a number to at least satisfy the valence state of the metals in the catalyst;

v) catalysts of the formula:

$$Mo_aV_rX_sY_tZ_uM_vO_f$$

wherein X is at least one of Nb and Ta; Y is at least one of Sb and Ni; Z is at least one of Te, Ga, Pd, W, Bi and Al; M is at least one of Be, Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the metals in the catalyst.

A non-limiting example of an ODH catalyst material that can be used in this disclosure is a mixed metal oxide having the formula $Mo_1V_{0.1-1}Nb_{0.1-1}Te_{0.01-0.2}X_{0-0.02}O_f$ wherein X is selected from Pd, Sb, Ba, Al, W, Ga, Bi, Sn, Cu, Ti, Fe, Co, Ni, Cr, Zr, Ca and oxides and mixtures thereof, and f is a number to satisfy the valence state of the metals present in the catalyst.

Another non-limiting example of an ODH catalyst material that can be used in this disclosure is a mixed metal oxide that includes Mo, V, O, and iron (Fe). The molar ratio of Mo to V can be from 1:0.25 to 1:0.50 or from 1:0.30 to 1:0.45, or from 1:0.30 to 1:0.35, or from 1:0.35 to 1:0.45. The molar ratio of Mo to Fe can be from 1:0.25 to 1:5.5, or from 1:3 to 1:5.5, or from 1:4.25 to 1:4.75, or from 1:4.45 to 1:4.55, or from 1:0.1 to 1:1, or from 1:0.25 to 1:0.75, or from 1:0.4 to about 1:0.6, or about 1:0.4, or about 1:0.6, or from 1:1.3 to 1:2.2, or from 1:1.6 to 1:2.0, or from 1:1.80 to 1:1.90. Further, oxygen is present at least in an amount to satisfy the valence state of the metals present in the catalyst. The catalyst can have at least a portion of the Fe in the catalyst material present as Fe(III). The catalyst can have at least a portion of the Fe in the catalyst material present as amorphous iron. The catalyst can have at least a portion of the Fe in the catalyst material present as an iron oxide, an iron oxide hydroxide, or a combination thereof. The iron oxide can include an iron oxide selected from hematite ($\alpha$-$Fe_2O_3$), maghemite ($\gamma$-$Fe_2O_3$), magnetite ($Fe_3O_4$), or a combination thereof. The iron oxide hydroxide can include an iron oxide hydroxide selected from a goethite, an akageneite, a lepidocrocite, or a combination thereof. The catalyst can include at least a portion of the iron as a goethite and at least a portion of the iron as a hematite.

A further non-limiting example of an ODH catalyst material that can be used in this disclosure is a mixed metal oxide having the empirical formula $Mo_1V_{0.25-0.5}O_d$ wherein d is a number to satisfy the valence state of the metals present in the catalyst. The molar ratio of Mo to V can be from 1:0.25 to 1:0.5, or 1:0.3 to 1:0.49.

A non-limiting example of an ODH catalyst material that can be used in this disclosure is a mixed metal oxide that includes Mo, V, O, and aluminum (Al). The molar ratio of Mo to V can be from 1:0.1 to 1:0.50, or from 1:0.25 to 1:0.50, or from 1:0.3 to 1:0.49, or from 1:0.30 to 1:0.45, or from 1:0.30 to 1:0.35, or from 1:0.35 to about 1:0.45. The molar ratio of Mo to Al is from 1:1.5 to 1:6.5, or from 1:3.0 to 1:6.5, or from 1:3.25 to 1:5.5.5, or from 1:3.5 to 1:4.1, or from 1:4.95 to 1:5.05, or from 1:4.55 to 1:4.65, or from 1:1.5 to 1:3.5, or from 1:2.0 to 1:2.2, or from 1:2.9 to 1:3.1. Oxygen is present at least in an amount to satisfy the valence state of the metals present in the catalyst. At least a portion of the Al in the catalyst material can be present as an aluminum oxide; the aluminum oxide can be an aluminum oxide hydroxide. The aluminum oxide hydroxide can include an aluminum oxide hydroxide selected from a gibbsite, a bayerite, a boehmite, or a combination thereof. At least a portion of the Al in the catalyst material can be present as gamma alumina.

Another non-limiting example of an ODH catalyst material that can be used in this disclosure is a mixed metal oxide that includes Mo, V, O, Al, and Fe. The molar ratio of Mo to V can be from 1:0.1 to 1:0.5, or from 1:0.30 to 1:0.45, or from 1:0.30 to 1:0.35, or from 1:0.35 to 1:0.45. The molar ratio of Mo to Al can be from 1:1.5 to 1:6.0. The molar ratio of Mo to Fe can be from 1:0.25 to 5:5. Oxygen is present at least in an amount to satisfy the valence state of the metals present in the catalyst. The molar ratio of Mo to Fe can be from 1:0.1 to 1:1, and the molar ratio of Mo to Al can be from 1:3.5 to 1:5.5. The molar ratio of Mo to Fe can be from 1:0.25 to 1:0.75, and the molar ratio of Mo to Al can be from 1:3.75 to 1:5.25. The molar ratio of Mo to Fe can be from 1:0.35 to 1:0.65, and the molar ratio of Mo to Al can be from 1:3.75 to 1:5.25. The molar ratio of Mo to Fe can be from 1:0.35 to 1:0.45, and the molar ratio of Mo to Al can be from 1:3.9 to 1:4.0. The molar ratio of Mo to Fe can be from 1:0.55 to 0:65, and the molar ratio of Mo to Al can be from 1:4.95 to 1:5.05. The molar ratio of Mo to Fe can be from 1:1.3 to 1:2.2, and the molar ratio of Mo to Al can be from 1:2.0 to 1:4.0. The molar ratio of Mo to Fe can be from 1:1.6 to 1:2.0, and the molar ratio of Mo to Al can be from 1:2.5 to 1:3.5. The molar ratio of Mo to Fe can be from 1:1.80 to 1:1.90, and the molar ratio of Mo to Al can be from 1:2.9 to 1:3.1. At least a portion of the Fe in the catalyst material can be present as Fe(III). At least a portion of the Fe in the catalyst material can be present as amorphous Fe. At least a portion of the Fe in the catalyst material can be present as an iron oxide, an iron oxide hydroxide, or a combination thereof. In some embodiments, the iron oxide includes an iron oxide selected from hematite ($\alpha$-$Fe_2O_3$), maghemite ($\gamma$-$Fe_2O_3$), magnetite ($Fe_3O_4$), or a combination thereof. Iron oxide hydroxide can include an iron oxide hydroxide selected from a goethite, an akageneite, a lepidocrocite, or a combination thereof. At least a portion of the Fe in the catalyst material can be present as a goethite and at least a portion of the Fe in the catalyst material can be present a hematite. At least a portion of the Al in the catalyst material can be is present as an aluminum oxide. The aluminum oxide can include an aluminum oxide hydroxide. The aluminum oxide hydroxide can include an aluminum oxide hydroxide selected from a gibbsite, a bayerite, a boehmite, or a combination thereof. At least a portion of the aluminum in the catalyst material can be present as a gamma alumina.

A further non-limiting example of an ODH catalyst material that can be used in this disclosure is a mixed metal oxide that includes Mo, V, Be, and O. The molar ratio of Mo to V can be from 1:0.25 to 1:0.65, or from 1:0.35 to 1:0.55, or from 1:0.38 to 1:0.48. The molar ratio of Mo to Be can be from 1:0.25 to 1:0.85, or from 1:0.35 to 1:0.75, or from 1:0.45 to 1:0.65. Oxygen is present at least in an amount to satisfy the valence state of the metals present in the catalyst.

A non-limiting example of an ODH catalyst material that can be used in this disclosure is a mixed metal oxide that includes Mo, V, Be, Al and O. The molar ratio of Mo to V can be from 1:0.25 to 1:0.65, or from 1:0.35 to 1:0.55, or from 1:0.38 to 1:0.48. The molar ratio of Mo to Be can be from 1:0.25 to 1:1.7, or from 1:0.35 to 1:0.75, or from 1:0.45 to 1:0.65. The molar ratio of Mo to Al can be from 1:1 to 1:9, or from 1:2 to 1:8, or from 1:4 to 1:6. Oxygen is present at least in an amount to satisfy the valence state of the metals present in the catalyst. At least a portion of the aluminum in the catalyst material can be present as an aluminum oxide. The aluminum oxide can include an aluminum oxide hydroxide. The aluminum oxide hydroxide can include an aluminum oxide hydroxide selected from a gibbsite, a bayerite, a boehmite, or a combination thereof. At least a portion of the aluminum in the catalyst material can be present as gamma alumina.

In many cases the ODH catalyst material that can be used in this disclosure has an amorphous phase of from 20 wt. % to 50 wt. %, or from 25 wt. % to 45 wt. %, or from 45 wt. % to 75 wt. %, or from 55 wt. % to 65 wt. %, or from 50 wt. % to 85 wt. %, or from 55 wt. % to 75 wt. %, or from 60 wt. % to 70 wt. %.

In many cases the ODH catalyst material that can be used in this disclosure has an average crystallite size of greater than 50 nm, or greater than 75 nm, or greater than 100 nm, or greater than 125 nm, or from 75 nm to 150 nm, or from 75 nm to 250 nm, or from 125 nm to 175 nm.

In many cases the ODH catalyst material that can be used in this disclosure has a mean particle size from 0.5 µm to 10 µm, or from 2 µm to 8 µm, or from 3 µm to 5 µm, or from 0.5 µm to 20 µm, or from 5 µm to 15 µm, or from 7 µm to 11 µm.

In many cases the ODH catalyst material that can be used in this disclosure is characterized by having at least one or more XRD diffraction peaks (2θ degrees) chosen from 6.5±0.2, 7.8±0.2, 8.9±0.2, 10.8±0.2, 13.2±0.2, 14.0±0.2, 22.1±0.2, 23.8±0.2, 25.2±0.2, 26.3±0.2, 26.6±0.2, 27.2±0.2, 27.6±0.2, 28.2±0.2, 29.2±0.2, 30.5±0.2, and 31.4±0.2 wherein the XRD is obtained using CuKα radiation. In other cases ODH catalyst material that can be used in this disclosure is characterized by having at least one or more XRD diffraction peaks (2θ degrees) chosen from 6.6±0.2, 6.8±0.2, 8.9±0.2, 10.8±0.2, 13.0±0.2, 22.1±0.2, 26.7±0.2, 27.2±0.2, and 28.2±0.2, where the XRD is obtained using CuKα radiation.

In many cases the ODH catalyst material that can be used in this disclosure includes from about 0.8 wt. % to about 30 wt. % calcium, in some instances about 0.15 wt. % to about 2.8 wt. % calcium. In some situations, the catalyst material can include about 0.5 wt. % to about 75 wt. % calcium carbonate, in some situations about 5 wt. % to about 15 wt. % calcium carbonate.

The catalyst may be supported on or agglomerated with a binder, carrier, diluent or promoter. Some binders include acidic, basic or neutral binder slurries of $TiO_2$, $ZrO_2$, $Al_2O_3$, AlO(OH) and mixtures thereof. Another useful binder includes $Nb_2O_5$. The agglomerated catalyst may be extruded in a suitable shape (rings, spheres, saddles, etc.) of a size typically used in fixed bed reactors. When the catalyst is extruded, various extrusion aids known in the art can be used. In some cases, the resulting support may have a cumulative surface area of as high as 300 m²/g as measured by BET, in some cases less than 35 m²/g, in other cases less than 20 m²/g, in other cases less than 3 m²/g, and a cumulative pore volume from 0.05 to 0.50 cm³/g.

The catalysts may be used alone or in combination with other materials. Also, in some embodiments the catalysts may be use with a promotor such ad Pd, Pt or Ru to increase the catalyst activity.

The mixed metal oxide catalyst can be a supported catalyst. The support may be selected from oxides of titanium, zirconium, aluminum, magnesium, yttrium, lanthanum, silicon, zeolites and clays and their mixed compositions or a carbon matrix. The mixed metal oxide catalyst can also have a binder added which increases cohesion among the catalyst particles and optionally improves adhesion of the catalyst to the support if present. The mixed metal oxide catalyst can be diluted with inert material, such as DENSTONE® 99 alumina particles or SS 316 particles.

EXAMPLES

Details of the disclosure will be described by reference to the following examples. The following examples are merely illustrative of the disclosure and are not intended to be limiting.

A fixed bed reactor unit (FBRU) was used to conduct experiments on manipulating the ODH product distribution by means of co-feeding different ratios of ethanol to steam. The FBRU apparatus consisted of two vertically arranged fixed bed tubular reactors in series, each reactor a SS316L tube with an outer diameter of 1" and a length of 34", wrapped in an electrical heating jacket and sealed with ceramic insulating material. Each reactor contained an identical catalyst bed consisting of one weight unit of catalyst to 2.14 units of weight of DENSTONE® 99 (mainly alpha alumina) powder. Total weight of the catalyst in each reactor was 143 g for examples 1-3, and 5, and 150 g for example 4. The catalyst was a mixed metal oxide of the formula $Mo_{1.0}V_{0.30-0.40}Te_{0.10-0.20}Nb_{0.10-0.20}O_X$, (as measured by particle-induced X-ray emission analysis, also known as "PIXE") in which X can be calculated based on the highest oxidation state of the metals present in this catalyst. The rest of the reactor, below and above the catalyst bed, was packed with quartz powder secured in place with glass wool to minimize risk of bed movement during the experimental runs.

The temperature of each of the reactors were monitored using corresponding 7-point thermocouples present in each reactor, 4 of which were situated within each catalyst bed. Temperature control, particularly at lower temperatures, was limited and resulted in fluctuations. Temperatures listed in the examples represents averages of the temperatures at the 8 different locations within the two catalyst beds. Both reactors were being controlled for temperature by controlling the pressure and boiling temperature of water inside water jackets surrounding each reactor.

For the experimental setup, a pressure transducer located immediately upstream of the first reactor was used to monitor the pressure at the inlet. The product stream leaving the second reactor was passed through condensing units before venting to air, which indicates that pressure at the point approximates 0 psig.

In the examples, ethane, ethylene, carbon dioxide, oxygen, nitrogen and liquid feed (water, alcohol or a mixture thereof) were fed separately (on as-needed basis) and premixed and heated to a temperature of greater than or equal to 220° C. before introduction in the FBRU. It was found that when ethanol was included with steam in a stream that was added to an ODH reactor producing ethylene, the addition of ethanol to the stream was found to both increase ethylene yield and decrease acetic acid yield. The addition of ethanol to the stream was found to have no effect on either CO or $CO_2$ yield, and have negligible effect on ethane conversion. The addition of ethanol to the stream was found to have a negligible effect on the ODH catalyst activity.

Example 1: Changing ODH Product Distribution by Varying the Feed Volumetric Ratio of Ethanol to Steam In order to explore the effect of feed volumetric ratio of ethanol to steam on ODH product distribution, a feed mixture of ethanol, steam, ethane, and oxygen was fed into the FBRU reactor with a fixed GHSV of 648 $h^{-1}$, a fixed reaction temperature of 319-324° C., and a fixed volumetric ratio of ethane:oxygen ($C_2H_6O_2$) of 4.0:1. The catalyst bed was diluted with DENSTONE® 99 alumina (Saint-Gobain NorPro). Three experiments, 1-1, 1-2, and 1-3, were conducted with variable feed volumetric ratios of ethanol to steam for the ethanol/steam stream, ranging from 0.01 to 0.10, by injecting different concentrations of ethanol in balance water into the reactor feed. The volumetric ratio of ethanol to steam and the combined feed compositions, the feed stream combined with the ethanol/steam stream, for each of the experiments are shown in Table 1.

TABLE 1

| | Feed Vol Ratio | Combined Feed Composition (vol %) | | | |
|---|---|---|---|---|---|
| Ex# | $C_2H_5OH:H_2O$ | $C_2H_5OH$ | $H_2O$ | $C_2H_6$ | $O_2$ |
| 1-1 | 0.10 | 0.78 | 7.51 | 73.38 | 18.32 |
| 1-2 | 0.04 | 0.78 | 17.43 | 65.45 | 16.35 |
| 1-3 | 0.02 | 0.78 | 37.66 | 49.26 | 12.30 |

The results of each of experiments 1-1, 1-2, and 1-3, are shown in Table 2. The results demonstrate that increasing the volumetric ratio of ethanol to steam increases ethane to ethylene selectivity, decreases acetic acid selectivity and yield, has a negligible effect on CO and $CO_2$ selectivity and yield and ethane conversion. The resulting ethane ODH product distribution was successfully altered in the direction of generating more ethylene and less acetic acid by co-feeding different feed volume ratios of ethanol to steam. No ethanol was detected in the product stream.

TABLE 2

| | Conversion | Yield (g compound/kg cat · hr) | | | | Selectivity (%) | | | |
|---|---|---|---|---|---|---|---|---|---|
| Ex # | (%) | $C_2H_4$ | $CO_2$ | CO | $CH_3COOH$ | $C_2H_4$ | $CO_2$ | CO | $CH_3COOH$ |
| 1-1 | 17 | 87 | 8 | 9 | 6 | 90.2 | 2.6 | 4.5 | 2.7 |
| 1-2 | 22 | 88 | 8 | 9 | 11 | 87.7 | 2.5 | 4.6 | 5.2 |
| 1-3 | 20 | 69 | 6 | 6 | 11 | 87.4 | 2.3 | 4.1 | 6.2 |

Example 2: Baseline Before and After Example 1 to Show No Catalyst Deactivation

The catalyst baseline activity was tested prior to and after conducting the experiments in Example 1, using identical conditions, to investigate whether the presence of ethanol and steam caused any catalyst deactivation. The operating conditions included a GHSV of 825 $h^1$, a reaction temperature of 325° C., a reactor inlet pressure of 19 psig, and a feed composition of 82 vol. % ethane and 18 vol. % oxygen. The results are shown in Table 3.

TABLE 3

| | Conversion | Ethane Yield | Selectivity (%) | | | |
|---|---|---|---|---|---|---|
| Ex # | (%) | (g $C_2H_4$/kg cat · hr) | $C_2H_4$ | $CO_2$ | CO | $CH_3COOH$ |
| Before Ex. 1 | 13 | 90 | 90 | 2 | 3 | 5 |
| After Ex. 1 | 15 | 120 | 91 | 1 | 3 | 4 |

Example 3: Removal of Residual $O_2$ in the Last Stage of an ODH Reactor by Reacting it with Ethanol The catalyst activity results show that the presence of ethanol and steam in the ODH feed had no detrimental effects on the catalyst and actually appeared to increase the catalyst activity.

In order to explore the effect of ethanol in removing residual $O_2$ from the last stage of an ODH reactor or within the product stream immediately downstream of the reactor, a feed composition predicted to be similar to the composition of the product stream from the last stage of an ODH reactor or within the product stream immediately downstream of the reactor, was fed to the FBRU at GHSV of 648 $h^{-1}$, at a temperature of 151-153° C., and an inlet reactor pressure of 13.3-13.9 psig for a duration of 29 hr:45 min. The catalyst bed was diluted with DENSTONE® 99 alumina. The composition of the feed and the product stream exiting the FBRU as a function of elapsed time, based on gas and liquid components, are shown in Table 4. While normally acetic acid would be found in the product stream immediately downstream of the reactor, for this experiment acetic acid was omitted because it was assumed that the presence of acetic acid would not have any impact on $O_2$ removal and also because the presence of acetic acid could mask the ethanol dehydration to acetic acid.

TABLE 4

|  | Gas Composition, Dry Basis (vol %) | | | | Liquid Composition (vol %) | | |
| --- | --- | --- | --- | --- | --- | --- | --- |
|  | $C_2H_6$ | $C_2H_4$ | $O_2$ | $CO_2$ | $C_2H_5OH$ | $H_2O$ | $CH_3COOH$ |
|  | Feed Composition | | | | | | |
| Feed | 11.0 | 87.9 | 0.6 | 0.6 | 13.6 | 85.9 | 0.0 |
| Elapsed Time (hh:mm) | Product Stream Composition | | | | | | |
| 5:10 | 10.7 | 88.7 | 0.0 | 0.7 | 2.4 | 93.3 | 4.3 |
| 21:15 | 10.4 | 89.0 | 0.0 | 0.6 | 2.4 | 93.3 | 4.3 |
| 30:00 | 10.9 | 88.5 | 0.0 | 0.6 | 2.4 | 93.3 | 4.3 |

The temperature of 151-153° C. was chosen because at that temperature the catalyst is not expected to convert ethane to ethylene. The data indicate that the ethanol in the feed was mainly converted to ethylene and acetic acid, and that all of the $O_2$ present in the feed was consumed. The $CO_2$ content in the feed and product stream remained virtually unchanged. The persistence of oxygen downstream of the ODH reactor can be problematic in subsequent processing steps, such as within an amine wash tower used for removal of carbon dioxide or within a cryogenic distillation unit where residual oxygen may cause fouling. The results show that use of ethanol within the feed to the ODH may be useful in removing residual oxygen from the final stage of the ODH reactor or within the product stream downstream of the reactor.

The catalyst activity towards ethanol conversion to ethylene and acetic acid is shown in Table 5, and demonstrates that catalyst activity was stable throughout.

TABLE 5

| Elapsed Time | Ethanol Conversion | Selectivity (%) | |
| --- | --- | --- | --- |
| (hh:mm) | (%) | $C_2H_4$ | $CH_3COOH$ |
| 5:10 | 87 | 68 | 32 |
| 21:15 | 87 | 68 | 32 |
| 30:00 | 87 | 68 | 32 |

Example 4: Effect of Ethanol Addition in the Presence of ODH Catalyst and SS 316 Diluent In order to understand the effect of feed ethanol on ODH product yield and distribution, two experiments were conducted using ODH catalyst diluted with stainless steel 316. During the experiments the FBRU operating conditions remained unchanged, with a GHSV of 648 $h^{-1}$, a temperature of 321° C., ambient inlet pressure (psig), and a feed volume ratio of ethane:oxygen of 4.0:1. The two experiments differed in that experiment 4-2 included 0.8 vol % feed ethanol (ratio of ethanol:steam was 0.10). The varied parameters are shown in Table 6. The ODH product yield and distribution for experiments 4-1 and 4-2 are shown in Table 7.

TABLE 6

| | | Variable Feed Parameters | | | | |
|---|---|---|---|---|---|---|
| | | Feed Vol Ratio | Feed Composition (vol %) | | | |
| Ex # | Catalyst | $C_2H_5OH:H_2O$ | $C_2H_5OH$ | $H_2O$ | $C_2H_6$ | $O_2$ |
| 4-1 | ODH + 316 SS | 0.00 | 0.0 | 8.3 | 73.4 | 18.3 |
| 4-2 | ODH + 316 SS | 0.10 | 0.8 | 7.5 | 73.4 | 18.3 |

TABLE 7

| | | Yield (g compound/kg cat · hr) | | | |
|---|---|---|---|---|---|
| Ex # | Conversion (%) | $C_2H_4$ | $CO_2$ | CO | $CH_3COOH$ |
| 4-1 | 29 | 92 | 9 | 12 | 27 |
| 4-2 | 30 | 95 | 8 | 11 | 25 |

The data from 4-1 and 4-2 indicate that addition of feed ethanol in an ODH process where the catalyst is diluted with stainless steel 316 provided an increase in ethane conversion, and that the increase is reflected in the increase in ethylene yield and a decrease in the yields of acetic acid, CO and $CO_2$.

Example 5: Effect of Ethanol Addition with ODH Catalyst and Denstone® 99 Alumina Diluent In order to understand the effect of feed ethanol on ODH product yield and distribution over ODH catalyst diluted with DENSTONE® 99 alumina, two experiments were conducted. During the experiments the FBRU operating conditions remained unchanged, with a GHSV of 648 h$^{-1}$, a temperature of 310-315° C., ambient inlet pressure (psig), and a feed volume ratio of ethane:oxygen of 4.0:1. The experiments differed in that experiment 5-2 included 0.8 vol % feed ethanol (ratio of ethanol:steam was 0.04). The varied parameters are shown in Table 8. The ODH product yield and distribution for experiments 5-1 and 5-2 are shown in Table 9.

TABLE 8

| | | Variable Feed Parameters | | | | |
|---|---|---|---|---|---|---|
| | | Feed Vol Ratio | Feed Composition (vol %) | | | |
| Ex # | Catalyst | $C_2H_5OH:H_2O$ | $C_2H_5OH$ | $H_2O$ | $C_2H_6$ | $O_2$ |
| 5-1 | ODH + Alumina | 0.00 | 0.0 | 18.2 | 65.7 | 16.2 |
| 5-2 | ODH + Alumina | 0.04 | 0.8 | 17.2 | 65.8 | 16.2 |

TABLE 9

| | | Yield (g compound/kg cat · hr) | | | |
|---|---|---|---|---|---|
| Ex # | Conversion (%) | $C_2H_4$ | $CO_2$ | CO | $CH_3COOH$ |
| 5-1 | 18 | 75 | 4 | 5 | 15 |
| 5-2 | 20 | 83 | 7 | 8 | 14 |

The data indicate that addition of feed ethanol into the ODH process where the catalyst is diluted with DENSTONE® 99 provided increases in the yields of ethylene, CO, and $CO_2$, and a decrease in acetic acid yield. The results from both Examples 4 and using different ODH catalyst additives (DENSTONE® 99 alumina, and stainless steel 316), in the presence of feed ethanol versus no feed ethanol, ethylene yield increased, and acetic acid yield decreased, while negligible increase in ethane conversion was observed. Use of DENSTONE® 99 alumina caused an increase in CO and $CO_2$ yields, whereas use of stainless steel 316 caused a decrease in CO and $CO_2$ yields. This implies that both of the mentioned additives can improve ethylene yield in the ODH process while feed ethanol is present.

The present invention has been described with reference to specific details of particular embodiments thereof. It is not intended that such details be regarded as limitations upon the scope of the invention except insofar as and to the extent that they are included in the accompanying claims.

INDUSTRIAL APPLICABILITY

The present disclosure relates to a process for the oxidative dehydrogenation of ethane. The process is applicable for altering product distribution and increasing ethylene yield by including ethanol and steam in the feed to the reactor.

The invention claimed is:

1. A process for increasing ethylene yield from an oxidative dehydrogenation (ODH) reactor system, the ODH reactor system comprising an ODH reactor, the ODH reactor containing a bed of mixed metal oxide catalyst, the process comprising:
    forming a feed stream comprising ethane and oxygen;
    forming an ethanol/steam stream comprising ethanol and steam;
    heating the ethanol/steam stream to a temperature above the dew point of ethanol;
    co-feeding the heated ethanol/steam stream and the feed stream as a combined feed to the ODH reactor; and
    contacting the combined feed with the mixed metal oxide catalyst under ODH conditions to form ethylene;
        wherein the combined feed comprises from 0.01 vol. % ethanol to 5.0 vol % ethanol;
        wherein the volumetric ratio of ethanol to steam in the combined feed is from 0.01 to 0.50; and
        wherein the ethylene yield is increased compared to the same process and oxidative dehydrogenation reactor system wherein the combined stream does not comprise ethanol.

2. The process according to claim 1, wherein the volumetric ratio of ethanol to steam in the combined feed is in the range of 0.02 to 0.10.

3. The process according to claim 1, wherein the combined feed comprises from 0.5 vol. % to 2 vol. % ethanol.

4. The process according to claim 1, wherein the combined feed comprises from 5 vol. % to 20 vol. % oxygen.

5. The process according to claim 1, wherein the combined feed comprises from 20 vol. % to 50 vol. % ethane.

6. The process according to claim 1, wherein the ODH reactor system comprises two ODH reactors.

7. The process according to claim 1, wherein the ODH reactor system comprises two mixed metal oxide catalysts.

8. The process according to claim 1, wherein the ODH conditions comprise a temperature from 310° C. to 350° C.

9. The process according to claim 1, wherein the ODH conditions comprise an inlet pressure from 15 psig to 50 psig.

10. The process according to claim 1, wherein the ODH conditions comprise a residence time from 0.1 to 10 seconds.

11. The process according to claim 1, wherein the ODH conditions comprise a gas hourly space velocity from 500 to 10,000 $h^{-1}$.

12. The process according to claim 1, wherein the feed stream is outside the flammability envelope.

13. The process according to claim 1, wherein the ethanol reacts with oxygen to form acetic acid.

14. The process according to claim 1, wherein the ethanol dehydrates to form ethylene.

15. The process according claim 1, wherein the process includes having a production rate of acetic acid that is decreased from a process in which only a feed stream is fed to the ODH reactor system.

16. The process according claim 1, wherein co-feeding the heated ethanol/steam stream with the feed stream to the ODH reactor system yields a production rate of acetic acid that remains the same as a process in which only the feed stream is fed to the ODH reactor system.

17. The process according to claim 1, wherein the mixed metal oxide catalyst comprises a mixed metal oxide selected from the group according to the formula:

$$Mo_1V_{0.1-1}Nb_{0.1-1}Te_{0.01-0.2}X_{0-0.2}O_f$$

wherein X is selected from Pd, Sb, Ba, Al, W, Ga, Bi, Sn, Cu, Ti, Fe, Co, Ni, Cr, Zr, Ca and oxides and mixtures thereof, and f is a number to satisfy the valence state of the metals present in the catalyst.

18. The process according to claim 1, wherein the mixed metal oxide catalyst is diluted with stainless steel, alumina or a combination thereof.

19. A process for the oxidative dehydrogenation (ODH) of ethane into ethylene comprising:
 providing a combined feed comprising ethane, oxygen, steam, and ethanol, to an ODH reactor;
 contacting the combined feed with an ODH catalyst in the ODH reactor under ODH conditions to form ethylene;
 wherein the combined feed comprises from 0.05 vol. % to 5 vol. % ethanol; and
 wherein the volumetric ratio of ethanol to steam in the combined feed is between from 0.01 to 0.50.

20. The process of claim 19 wherein ethylene yield is increased compared to a similar process where the combined feed does not contain ethanol.

21. The process according to claim 19, wherein the combined feed is heated to a temperature above the dew point of ethanol before contacting the ODH catalyst.

22. The process according to claim 19, wherein the combined feed is outside the flammability limits.

23. The process according to claim 19, wherein the combined feed comprises from 5 vol. % to 20 vol. % oxygen.

24. The process according to claim 19, wherein the combined feed comprises from 20 vol. % to 50 vol. % ethane.

25. The process according claim 19, wherein the combined feed comprises from 0.5 vol. % to 2 vol. % ethanol.

26. The process according to claim 19, wherein the ODH conditions comprise a temperature of from 300° C. to 400° C.

27. The process according to claim 19, wherein the ODH conditions comprise an inlet pressure of from 15.0 psig to 50 psig.

28. The process according to any of claims 19 through 25, wherein the residence of the ODH reactor is from 0.1 seconds to 10 seconds.

29. The process according to claim 19, wherein the ODH conditions comprise a gas hourly space velocity of from 500 $h^{-1}$ to 6,000 $h^{-1}$.

30. The process according to claim 19, wherein the ODH conditions comprise a linear velocity of from 10 cm/sec to 200 cm/sec.

31. The process according to claim 19, wherein the ODH conditions comprise a weight hourly space velocity of 2.0 $h^{-1}$ to 10 $h^{-1}$.

32. The process according to claim 31, wherein the mixed metal oxide catalyst comprises a mixed metal oxide selected from the group according to the formula:

$$Mo_1V_{0.1-1}Nb_{0.1-1}Te_{0.01-0.2}X_{0-0.2}O_f$$

wherein X is selected from Pd, Sb, Ba, Al, W, Ga, Bi, Sn, Cu, Ti, Fe, Co, Ni, Cr, Zr, Ca and oxides and mixtures thereof, and f is a number to satisfy the valence state of the metals present in the catalyst.

* * * * *